United States Patent
Deshpande et al.

(12)

(10) Patent No.: US 6,649,753 B2
(45) Date of Patent: Nov. 18, 2003

(54) STABLE SALTS OF S-ADENOSYL-L-METHIONINE (SAME) AND THE PROCESS FOR THEIR PREPARATION

(75) Inventors: Pandurang Balwant Deshpande, Tamil Nadu (IN); Udayampalam Palanisamy Senthilkumar, Tamil Nadu (IN); Subramaniam Ganesan, Tamil Nadu (IN)

(73) Assignee: Orchid Chemicals & Pharmaceuticals Ltd., Tamil Nadu (IN)

( * ) Notice: Subject to any disclaimer, the term of this patent is extended or adjusted under 35 U.S.C. 154(b) by 82 days.

(21) Appl. No.: 09/875,006

(22) Filed: Jun. 7, 2001

(65) Prior Publication Data

US 2003/0032796 A1 Feb. 13, 2003

(51) Int. Cl.$^7$ .................. C07H 19/167; C12P 19/40; C12P 13/12
(52) U.S. Cl. ............... 536/27.31; 536/27.3; 536/27.23; 536/27.2; 536/27.21; 536/27.1; 536/27.13; 435/88; 435/87; 435/85; 435/84; 435/113
(58) Field of Search .................. 536/27.31, 27.1, 536/27.13, 27.2, 27.21, 27.23, 27.3; 435/85, 113, 256, 88, 83, 84, 87; 424/180, 181

(56) References Cited

U.S. PATENT DOCUMENTS

| 3,954,726 A | 5/1976 | Fiecchi |
| 4,028,183 A | 6/1977 | Fiecchi |
| 4,057,686 A | 11/1977 | Fiecchi |
| 4,558,122 A | * 12/1985 | Gennari .................. 536/27.31 |
| 4,621,056 A | * 11/1986 | Gennari .................. 435/85 |
| 5,128,249 A | 7/1992 | Gennari |

FOREIGN PATENT DOCUMENTS

| EP | 0 072 980 | 3/1983 |
| EP | 0 073 376 | 3/1983 |
| FR | 2 275 220 | 6/1974 |
| JP | 52-48691 | 4/1977 |
| JP | 53-107485 | 9/1978 |
| JP | 58-49398 | 3/1983 |
| JP | 59-51213 | 3/1984 |
| JP | 60-181095 | 9/1985 |
| JP | 61-91125 | 5/1986 |
| WO | 89/03389 | 4/1989 |

OTHER PUBLICATIONS

Shelly C. Lu; S–Adenosylmethionine; The International Journal of Biochemistry & Cell Biology 32 (2000) 391–395; Sep. 27, 1999; pp. 391–395; Elsevier Science Ltd;.

* cited by examiner

Primary Examiner—James O. Wilson
Assistant Examiner—Josephine Young
(74) Attorney, Agent, or Firm—Burns, Doane, Swecker & Mathis, L.L.P.

(57) ABSTRACT

This invention relates to the production of new & stable salts of S-adenosyl-L-methionine SAMe). The source of SAMe used in the salt formation is from chemical process wherein stereoselective methylation of S-adenosyl-L-homocysteine is achieved. The process for the salt preparation is simple, efficient & reproducible on large scale. The new salts were found to be stable at accelerated temperature for minimum 3 months.

3 Claims, No Drawings

STABLE SALTS OF S-ADENOSYL-L-METHIONINE (SAME) AND THE PROCESS FOR THEIR PREPARATION

FIELD OF THE INVENTION

This invention relates to stable and new salts of S-adenosyl-L-methionine, which in turn is synthesized by a novel chemical method. The novel compounds of the invention are found to be more stable compared to the commonly available SAMe disulfate monotosylate and SAMe butane-1,4-disulfonate salts. The acute toxicity studies on the said salts have been successful and therefore, the salts are potential therapeutic agents.

BACKGROUND OF THE INVENTION

S-adenosyl-L-methionine, known as SAMe, is the main biological donor of methyl groups and it has several important therapeutic applications. As a substance existing in the living body, SAMe has been found to possess various pharmacological actions such as improvement of energy state of ischemic brain, improvement of cerebral energy metabolism and acidosis of the model with recirculated blood flow following ischemia, etc. SAMe is an important molecule in normal cell function and its survival. SAMe is utilized by three key metabolic pathways: trans-methylation, trans-sulfuration and polyamine synthesis. Given the importance of SAMe in tissue function, it is not surprising that this molecule is being investigated as a possible therapeutic agent for the treatment of various clinical disorders (Int. J. Biochem. Cell Biol. (2000), 32(4), 391–395).

PRIOR ART

The main problem associated with the large-scale use of S-adenosyl-L-methionine is its thermal instability even at ambient temperature, and its preparation and purification complexity. Thus, the said product has been the subject of numerous patents aimed at providing new stable salts as well as process for preparation of these salts.

While numerous salts of SAMe have been reported, most of them suffered the disadvantage of stability at accelerated temperature and the practicability for the large scale manufacturing. In some of the disclosures, use of various organic & inorganic stabilizers were reported but most of them could not give the required effect or they are not suitable for the large scale manufacturing. SAMe butane-1,4-disulphonate as disclosed in U.S. Pat. Nos. 3,954,726 & 4,028,183 has shown better stability & is being produced on large scale: Hence it was taken as the referral point for the comparison of stability.

Some of the known salts of SAMe & the stabilizers used in the process are as under. The data published in Res. Disclo. (1991), 332, 927–933 has reported the carboxylic acid salts of SAMe like gallic acid, ascorbic acid & maleic acid. EP 73376 & 72980 discloses the hydrochloride, phosphate, sulfate & methane sulfonate salts. In JP 53107485 salts of SAMe adsorbed on the resin were prepared by eluting with various organic acids originating from ethane, bromoethane, benzene, naphthalene, p-toluene, etc. FR 2275220 discloses the citrate, tartarate, maleate & ascorbate salts of SAMe.

U.S. Pat. No. 5,128,249 disclosed the SAMe salts of dioctylsulphosuccinic acid, or of sulphonic acids or esters of sulphuric acids wherein the sulphonic acids or the esters of sulphuric acids are derived from long-chain linear or branched alkyl moiety containing 8–18 carbons atoms, and as a consequence of such a high molecular weight and high mole ratio, the content of these organic acids in the said salt goes upto 62–76%.

JP 58049398 has reported the hydrochloride & sulfate salt which are stabilized by using magnesium salts as additive.

WO 89/03389 reported SAMe salts with high molecular weight oleyl and arachidonyl derivatives of taurine in a molar ratio of 1:>4.2 which therefore results in a very low content of SAMe in the said salt.

JP 59051213 has reported lactose as stabilizer while JP 52048691 has reported the use of lithium salts as stabilizer.

JP 60181095 & JP-Sho 61-91125 have reported the use of cyclodextrins as a stabilizer & clearly reported the poor stability of the common haloacid salts of SAMe (like chloride, bromide, iodide, etc.) as well as the SAMe base. It has further disclosed the irritating characteristics of the salts reported so far, their high moisture sensitivity, poor storage stability, cost of the acids and their availability for commercial use, and the manufacturing difficulties due to which none of them are used as a therapeutic agents.

Thus, there exists a need in the prior art to develop non-toxic new salts of SAMe which are stable at accelerated temperatures and further are equally or more stable as compared to butane-1,4-disulfonic acid salt. The applicants of the present invention, therefore, carried out intense investigation on a variety of systems in order to improve the storage stability of S-adenosyl-L-methionine. The study includes the effect of different type of acids, particularly, the sulphinic acids, and sulphonic acids—mono-, di-, tri sulphonic acids on aromatic or aliphatic systems, and the effect of the relative positions between them, like ortho-, meta-, or para-. Also, studies are the effects of the position of these acid functions with respect to other functional groups in the aromatic ring which could be ortho-, meta- or para-. The applicants also studied the effect of different types of one or more substituents on the aromatic ring at various positions relative to the sulphonic acid functionality. The applicants found the involvement of the nature and type of the substituent pattern of the protonic as well as aprotic functional groups in influencing the stability of the SAMe salt. The extensive study on a wide range of molecular systems led finally to improve the stability of the SAMe, and the features which form the subject matter of the present invention are discussed below.

DETAILED DESCRIPTION OF THE INVENTION

Accordingly, the invention provides three novel salts of SAMe, which are highly stable even at accelerated temperatures.

The applicant has identified a group of novel salts of SAMe which are not reported so far and the applicant found that these salts of some have better stability improves the stability of SAMe to a better level. These are i) SAMe disulfate resorcinol-4,6-disulfonate or its sodium salt; ii) SAMe disulfate catechol-3,5-disulfonate or its sodium salt; iii) SAMe disulfate phenol-2,4,6-trisulfonate or its sodium salt. However, the SAMe disulfate salt with analogous hydroquinone-2,3-disulphonic acid or its sodium salt was found to have poor stability at accelerated temperatures.

The process for the preparation of SAMe is disclosed in the Applicants' co-pending U.S. patent application Ser. No. 09/875,044, dated Jul. 6, 2001, filed concurrently herewith. The said process is a first ever report on the chemical synthesis of SAMe with enrichment of (S,S)-isomer to the extent of 60–65%.

Broadly, the said process comprises the steps of:

(a) reacting adenosine with thionyl chloride and pyridine at a temperature in the range of 30–35° C. to obtain 5'-chloromethyl adenosine hydrochloride, (b) treating L-methionine with sodium metal in the presence of water and liquid ammonia at −30 to −40° C. to obtain aqueous solution of L-homocysteine sodium salt, (c) condensing 5'-chloromethyl adenosine hydrochloride with L-homocysteine in the presence of water and potassium iodide at 70 to 80° C. to obtain S-adenosyl-L-homocysteine (SAH), and (d) subjecting SAH to methylation using trimethyloxonium tetrafluoroborate (TMOTFB) as a methylating agent in the presence of trifluoroacetic acid (TFA) as a solvent to obtain pure S-adenosyl-L-methionine enriched with (S,S)-isomer in the ratio 60 to 65%.

The required sulfonic acids are prepared by conventional methods and used in situ to react with SAMe. The aqueous salt solution obtained thereof is spray-dried to obtain the novel salts of the invention.

Production of SAMe Disulfate Resorcinol-4,6-disulfonate

The SAMe obtained by the process described herein above is treated with dilute sulphuric acid and resorcinol-4,6-disulfonic acid or its suitable sodium salt to obtain SAMe disulfate resorcinol-4,6-disulfonate or its sodium salt. The product so obtained is spray-dried.

Production of SAMe Disulfate Catechol-3,5-disulfonate

The SAMe obtained by the process described herein above is treated with dilute sulphuric acid and catechol-3,5-disulfonic acid or its suitable sodium salt to obtain SAMe disulfate catechol-3,5-disulfonate or its sodium salt. The product so obtained is spray-dried.

Production of SAMe Disulfate Phenol-2,4,6-trisulfonate

In order to produce SAMe disodium disulfate phenol-2,4,6-trisulfonate, SAMe is treated with dil.sulphuric acid and phenol-2,4,6-trisulfonic acid or its suitable sodium salt to obtain SAMe disulfate phenol-2,4,6-trisulfonate or its sodium salt. The product so obtained is spray-dried.

Assessment of stability of the above SAMe salts has been done as per the ICH guidelines at 40–45° C. with 70–75% Relative Humidity and an improved HPLC method has been employed which resolves all the impurities formed on degrading SAMe (Table I). This method of HPLC analysis is the best method known so far to study stability of SAMe and has been validated as per the ICH guidelines. The details of the HPLC method followed and the accelerated stability report are as under:

Column=YMC-ODS-A, 4.6 mm×25 cm, C-18, 5 micron

Buffer=A mixture of 0.02 M citric acid & 0.01 M sodium dihydrogen orthophosphate Mobile phase=using acetonitrile water with citric acid buffer Detector=UV at 254 nm wavelength Flow rate=1.5 ml per min.

Column temperature=25° C.

Accelerated Stability

The percentage of SAMe after storage at the specified temperature was determined using the content of SAMe after storage and the content of SAMe before storage, i.e., initial content of SAMe in the corresponding salt using the following equation:

$$\text{Residual Ratio of SAMe(\%)} = \frac{\text{SAMe(\%) after storage at specified time and temperature}}{\text{SAMe(\%) at the time of storage}} \times 100$$

TABLE I

Accelerated Stability Data for New SAMe Salts

| Accelerated Storage Period | SAMe Residual Ratio for* | | |
|---|---|---|---|
| | Salt I | Salt II | Salt III |
| 30 days | 97.7 | 97.5 | 98.0 |
| 60 days | 95.5 | 95.2 | 96.3 |
| 90 days | 95.0 | 94.5 | 95.8 |

*Salts I, II and III are disulphate salts of SAMe with salts of resorcinol-4,6-disulphonic acid, catechol-3,5-disulphonic acid, and phenol-2,4,6-trisulphonic acid, respectively. It is seen from the table that the extent of degradation is in the downward trend with time.

The process for producing SAMe salts according to the present investigation is characterized by (i) conversion of S-adenosyl-L-homocysteine into (S,S)-isomer enriched-SAMe, (ii) production of SAMe as SAMe sulphate salt, during product isolation, (iii) finally conversion into the required SAMe mixed sulfate and spray-drying.

These and further characteristics and advantages of the SAMe salts according to the present invention and the relative production process will be more apparent from the detailed description given hereinafter which relates to preferred method of implementing various stages of the process.

The hydroxy aromatic sulfonic acids are either available commercially or can be easily prepared from the corresponding aromatic hydrocarbons & used in situ.

The process for the manufacture of SAMe and its salts according to the present invention are conducted in the following manner:

In order to make the process according to the present invention more easily reproducible and to illustrate some of the advantages and simplicity of the process, some practical examples are given hereinafter for purely illustrative purposes, but which in no case limit the scope of the invention.

EXAMPLE 1

Preparation of SAMe Disulfate Resorcinol-4,6-disulfonate or its Sodium Salt

S-Adenosyl-L-homocysteine (1.0 Kg) was dissolved in trifluoroacetic acid (9.0 Lit) and cooled to −10±2° C. To this solution, conc.sulphuric acid (0.4 Lit) was added. Trimethyloxonium tetrafluoroborate (0.45 Kg) was added in 1 h and maintained at this temperature for 3.5 h. The temperature was raised to −5 to 0° C. and maintained for 2 h until HPLC indicated the absence of S-adenosyl-L-homocysteine. The solvent was removed under vacuum at <30° C. until a residue was obtained. Into the residue, chilled dil.sulphuric acid (6%; 2.0 Lit) was added to get a clear solution. Methanol (10.0 Lit) was added and the precipitated product was filtered under nitrogen atmosphere.

The filtered solid was dissolved in water (2.0 Lit) at 0–5° C. and methanol (10.0 Lit) was added. The precipitate obtained was filtered under nitrogen atmosphere. The solid was dissolved in water (2.0 Lit) at 0–5° C. and washed with dichloromethane (2×5.0 Lit) at the same temperature. The solution was degassed for 30 min and quantified for sulphate content. To the solution, required amount of dilute sulphuric acid and resorcinol-4,6-disulfonic free acid or its suitable sodium salt were added. The solution was spray-dried with air at 140–160° C.

Yield: 1.4 to 1.6 Kg.
HPLC Purity: 97.5–98.0%

EXAMPLE 2
Preparation of SAMe Disulfate Catechol-3,5-disulfonate or its Sodium Salt S-Adenosyl-L-homocysteine (1 Kg) was dissolved in trifluoroacetic acid (9.0 Lit) and cooled to −10±2° C. To the solution, conc.sulphuric acid (0.4 Lit) was added. Trimethyloxonium tetrafluoroborate (0.45 Kg) was added in 1 h and maintained at this temperature for 3.5 h. The temperature was again raised to −5 to 0° C. and maintained for 2 h until HPLC indicated the absence of S-adenosyl-L-homocysteine. The solvent was removed under vacuum at <30° C. until a residue was obtained. Into the residue, chilled dil.sulphuric acid (6%; 2.0 Lit) was added to get a clear solution. Methanol (10.0 Lit) was added and the precipitated product was filtered under nitrogen atmosphere.

The filtered solid was dissolved in water (2.0 Lit) at 0–5° C. and methanol (10.0 Lit) was added. The precipitate obtained was filtered under nitrogen atmosphere. The solid was dissolved in water (2.0 Lit) at 0–5° C. and washed with dichloromethane (2×5.0 Lit) at the same temperature. The solution was degassed for 30 min and quantified for sulphate content. To the solution, required amount of dil.sulphuric acid and catechol-3,5-disulfonic free acid or its suitable sodium salt were added. The solution was spray-dried with air at 140–160° C.

Yield: 1.4 to 1.6 Kg.
HPLC Purity: >98.0%.

EXAMPLE 3
Preparation of SAMe Disulfate Phenol-2,4,6-trisulfonate or its Sodium Salt S-Adenosyl-L-homocysteine (1 Kg) was dissolved in trifluoroacetic acid (9.0 Lit) and cooled to −10±2° C. To the solution, conc.sulphuric acid (0.4 Lit) was added. Trimethyloxonium tetrafluoroborate (0.45 Kg) was added in 1 h and maintained at this temperature for 3.5 h. The temperature was raised to −5 to 0° C. and maintained for 2 h until HPLC indicated the absence of S-adenosyl-L-homocysteine. The solvent was removed under vacuum at <30° C. until a residue was obtained. Into the residue, chilled dil.sulphuric acid (6%; 2.0 Lit) was added to get a clear solution. Methanol (10.0 Lit) was added and the precipitated product was filtered under nitrogen atmosphere.

The filtered solid was dissolved in water (2.0 Lit) at 0–5° C. and methanol (10.0 Lit) was added. The precipitate obtained was filtered under nitrogen atmosphere. The solid was dissolved in water (2.0 Lit) at 0–5° C. and washed with dichloromethane (2×5.0 Lit) at the same temperature. The solution was degassed for 30 min and quantified for sulphate content. To the solution, required amount of dil.sulphuric acid and phenol-2,4,6-trisulfonic free or its suitable sodium salt were added. The solution was spray-dried with hot air at 140–160° C.

Yield: 1.4 to 1.6 Kg.
HPLC Purity: 97.5–98.5%

What is claimed is:

1. A stable salt of S-adenosyl-L-methionine selected from the group consisting of S-adenosyl-L-methionine disulfate resorcinol-4,6-disulfonate, S-adenosyl-L-methionine disulfate catechol-3,5-disulfonate, S-adenosyl-L-methionine disulfate phenol-2,4,6-trisulfonate and a sodium salt thereof.

2. A process for preparing a stable salt of claim 1, the process comprising:
   i) converting S-adenosyl-L-homocysteine into (S-S)-isomer enriched-S-adenosyl-L-methionine;
   ii) producing S-adenosyl-L-methionine as a S-adenosyl-L-methionine sulfate salt; and
   iii) converting the S-adenosyl-L-methionine sulfate salt into a S-adenosyl-L-methionine mixed sulfate salt and spray drying it.

3. The process of claim 2, wherein the conversion step (iii) is conducted using a sulphonic acid selected from the group consisting of resorcinol-4-6-disulfonic acid, catechol-3,5-disulfonic acid and phenol-2,4,6-trisulfonic acid.

* * * * *